United States Patent [19]

Young

[11] Patent Number: 4,729,999
[45] Date of Patent: Mar. 8, 1988

[54] ANTIESTROGEN THERAPY FOR SYMPTOMS OF ESTROGEN DEFICIENCY

[75] Inventor: Ronald L. Young, Houston, Tex.

[73] Assignee: BCM Technologies, The Woodlands, Tex.

[21] Appl. No.: 660,510

[22] Filed: Oct. 12, 1984

[51] Int. Cl.$^4$ .................. A61K 31/535; A61K 31/445; A61K 31/40; A61K 31/19

[52] U.S. Cl. ..................................... 514/227; 514/317; 514/408; 514/569; 514/646; 514/731; 514/899

[58] Field of Search ............... 514/646, 227, 317, 408, 514/569, 731, 899

[56] References Cited

U.S. PATENT DOCUMENTS

| | | | |
|---|---|---|---|
| 2,914,562 | 10/1959 | Allen | 260/570 |
| 2,914,563 | 10/1959 | Allen | 260/570 |
| 2,914,564 | 10/1959 | Allen | 260/570 |
| 3,634,517 | 1/1972 | Palopoll et al. | 260/590 |
| 3,697,581 | 10/1972 | Humber | 260/240 R |
| 3,843,727 | 10/1974 | Humber | 260/270.7 |
| 4,061,733 | 12/1977 | Gurjikar | 424/143 |

OTHER PUBLICATIONS

C. Hammond, M.D. et al., "Current Status of Estrogen Therapy for the Menopause," *Fertil. Steril.* 37(1):5-25 (1982).

J. Gallagher, et al., "Epidemiology of Fractures of the Proximal Femur in Rochester, Minnesota," *Clin. Ortho.* 150:163–171 (1980).

Boston Collab. Drug Surv. Program, "Surgically Confirmed Gallbladder Disease, Venous Thromboembolism, and Breast Tumors in Relation to Postmenopausal Estrogen Therapy," *N. Eng. J. Med.* 290(1):15-19 (1974).

M. Crane, M.D., et al., "Hypertension Oral Contraceptive Agents, and Conjugated Estrogens," *Ann. Int. Med.* 74(1):13-21 (1971).

R. Pfeffer, "Estrogen Use, Hypertension and Stroke in Postmenopausal Women," *J. Chron. Dis.* 31:389–398 (1978).

M. Notelovitz, "Metabolic Effect of Conjugated Oestrogens (USP) on Glucose Tolerance," *So. African Med. J.* 48(4):2599–2603 (1974).

J. Stangel, et al., "The Effect of Conjugated Estrogens on Coagulability in Menopausal Women," *Obstet. Gynecol.* 49(3):314–316 (1977).

T. Gordon, et al., "Menopause and Coronary Heart Disease," *Ann. Int. Med.* 89(2):157–161 (1978).

A. Kauppila, et al., "Comparison of Megestrol Acetate and Clomiphene Citrate as Supplemental Medication in Postmenopausal Oestrogen Replacement Therapy," *Arch. Gynecol.* 234:49–58 (1983).

A. Kaupilla, M.D., et al., "Postmenopausal Hormone Replacement Therapy with Estrogen Periodically Supplmented with Antiestrogen," *Am. J. Obstet. Gynecol.* 140(7):787–792 (1981).

A. Wise, et al., "Quantitative Relationships of the Pituitary-Gonadal Axis in Postmenopausal Women," *J. Lab. Clin. Med.* 81(1):28–36 (1973).

E. Su-Rong Huang, et al., "Estrogenic and Antiestrogenic Effects of Enclomiphene and Zuclomiphene on Gonadotropin Secretion by Ovine Pituitary Cells in Culture," *Endocrinol.* 112(2):442–448 (1983).

A. Mukku, et al., "Stimulatory and Inhibitory Effects of Estrogen and Antiestrogen on Uterine Cell Division," *Endocrinol.* 109(4):1005–1010 (1981).

M. Sankaran and M. Prasad, "A Critique on the Evaluation and Mode of Action of Antiestrogens," *Horomones and Antagonists. Gynec. Invest.* 3:143–147 (1972).

L. Terenius, et al., "Aspects on the Mode of Action of Antiestrogens and Antiprogestogens," *Horomones and Antagonists. Gynec. Invest.* 3:96–107 (1972).

C. Geynet, et al., "Estrogens and Antiestrogens," *Hormones and Antagonists. Gynec. Invest.* 3:2–29 (1972).

J. Wood, et al., "Estrogenic and Antiestrogenic Effects of Clomiphene, MER-25 and CN-55,945-27 on the Rat Uterine and Vagina," *Endocrinol.* 82:69–74 (1968).

K. Schulz, et al., "Studies on Anti-Oestrogenic and Oestrogen-Like Action of Clomiphene Citrate—Animal Experiments," *Hormones and Antagonists. Gynec. Invest.* 3:135–141 (1972).

J. Clark, et al., "The Agonistic-Antagonistic Properties of Clomiphene: A Review," *Pharmac. Ther.* 15:467–519 (1982).

M. Pugeat, et al., "On the Testing the Treshold of Sensitivity of the Gonadostat in the Late Menopausal Period: Effect of the Administration of Clomiphene Citrate or Ethynylestradiol on Plasma Levels of Gonadotropin, Testosterone and Delta-4 Antostendione," *Eur. J. Obstet. Gynecol. Reprod. Biol.* 9(3):218–219 (1979).

M. Zambrano, et al., "Evaluation of the Action of Clomiphene Citrate (Clomid) on Mouse Chromosomes by the Metaphase and Micronucleus Tests," *Rev. Brasil. Genet.* 2:339–344 (1982).

J. Gennes, et al., "Clinical, Biological, Histological and Genetic Studies of De Morsier's Syndrome (Hypogonadotrophic Hypogonadism with Anosmia)," *Ann. Endocrinol.* 31(5):841–861 (1970).

I. Spitz, et al., "The Decreased Basal and Stimulated Prolactin Levels in Isolated Gonadotrophin [sic] Deficiency: A Consequence of the Low Oestrogen State," *Clin. Endocrinol.* 16:423–432 (1982).

(List continued on next page.)

Primary Examiner—J. R. Brown
Assistant Examiner—John W. Rollins, Jr.
Attorney, Agent, or Firm—Eric P. Mirabel

[57] ABSTRACT

The invention involves a method for treating symptoms secondary to estrogen deficiency without using estrogen. Weakly estrogenic antiestrogens are administered to estrogen deficient women in the absence of estrogen administration. Maximum estrogenic activity is therby obtained and the harmful side effects of estrogen therapy are avoided.

29 Claims, No Drawings

OTHER PUBLICATIONS

S. Aksel, M.D., et al., "Etiology and Treatment of Dysfunctional Uterine Bleeding," *J. Obstet. and Gynec.* 44(1):1—13 (1974).

T. Hashimoto, M.D., et al., "Endocrinological Study of Patients with Meningitis Tuberculosa," *Jap. J. Med.* 20(1):45-49 (1981).

C. March, M.D., "Effect of Pretreatment with Clomiphene Citrate Upon Human Menopausal Gonadotropin Therapy for Anovulation," *Fertil. Steril.* 26(2):191-192 (1975).

T. Hashimoto, M.D., et al., "Dual Effect of Clomiphene Citrate on Pituitary Gonadotropin Secretion in Postmenopausal Women," *Endocrinol. Jap.* 23(2):115-118 (1976).

T. Nencioni, et al., "Plasma FSH, LH and Prolactin Levels in Postmenopausal Women Undergoing Cyclofenil [sic] Treatment," *Acta Obstet. Gynecol. Scand.* 61:487-490 (1982).

R. Young, et al., "Antiestrogen Effects on Gonadotropins and Uterus in the Ovariectomized Rat," *Abstracts of the Endocrine Society* #142, p. 108 (1979).

M. Pugeat, et al., "Effects of Clomiphene and Estrogens on Circulating Gonadotropins, Testosterone, Androstenedione, in Old Menopausal Women," *Ann. Endocrinol.* 38:363-365 (1977).

A. LeBlanc, et al., "Effects of Clomiphene on Total Body Calcium in Aged Oophorectomized Rats," *Calcium, Calcium Hormones*, Abstract #7738, p. 1594 (1982).

H. Kupperman, et al., "Comparative Clinical Evaluation of Estrogenic Preparations by the Menopausal and Amenorrheal Indices," *J. Clin. Endo.* 13:688-703 (1953).

ANTIESTROGEN THERAPY FOR SYMPTOMS OF ESTROGEN DEFICIENCY

BACKGROUND OF THE INVENTION

This invention relates to therapeutic processes, and more particularly to a process for treating human postmenopausal symptoms.

Women in the postmenopausal age range now number approximately 40,000,000 in the United States alone, and each of these women faces an average life expectancy of 28 years beyond the last menstrual period. A recent review estimates that 75% to 85% of postmenopausal women will develop symptoms secondary to estrogen deficiency. C. Hammond, M.D., et al., "Current Status of Estrogen Therapy for the Menopause," *Fertil. Steril*, 37(1):5–25 (1982).

Perhaps the most common group of complaints of the patient following ovarian failure is the vasomotor symptom complex. The "hot flash" is classically described as a sudden onset of warmth in the face and neck which usually progresses to the chest. This sensation generally lasts several minutes and is often accompanied by a visible red flush. These episodes may be exceedingly uncomfortable and are frequently associated with dizziness, nausea, headaches, palpitations and diaphoresis. Estrogen supplementation will provide significant relief in over 90% of such patients.

Progressive atrophy of the genitourinary system commonly accompanies old age and is related both to estrogen deprivation and to the normal aging process. The vagina, cervix, corpus uteri, fallopian tubes, urethra and bladder trigone all have large numbers of estrogen receptors and are sensitive to a decrease in available estrogen. The vagina exhibits marked atrophic changes secondary to estrogen deprivation, characterized by thinning of the epithelium, loss of rugation and a reduction in lubrication during sexual intercourse. Atrophic vaginitis accounts for approximately 15% of postmenopausal bleeding and contributes significantly to dyspareunia.

Atrophy of the urethra in general parallels similar changes in the vagina. A significant consequence of urethral atrophy is the occurrence of dysuria, frequency of urination and urinary urgency. Systemic or intravaginal estrogen therapy dramatically reverses the atrophic process. The most serious of all postmenopausal complications is osteoporosis. In women over 60 years of age, 25% have documented spinal compression fractures as a result of osteoporosis. As many as 50% of women will have developed vertebral fractures by age 75. The risk of hip fractures increases with age and reaches 20% by age 90. Eighty percent (80%) of hip fractures are felt to be related to pre-existing osteoporosis. Even more devastating is the fact that approximately one-sixth of women with hip fractures die within three months following their fracture. A Mayo Clinic study calculates the health care costs of fracture hospital stays at over $1,000,000,000 per year. J. Gallagher, et al., "Epidemiology of Fractures of the Proximal Femur in Rochester, Minn., "*Clin. Ortho.* 150:163–171 (1980).

Numerous mechanisms for postmenopausal osteoporosis have been proposed, tested and reviewed. Current theories include contributions of dietary factors and calcium intake, aging, genetic susceptibility, Vitamin D status and the hormone control of bone deposition and absorption including roles for estrogen, androgens, parathyroid hormones, growth hormones and calcitonin.

Current treatment for postmenopausal osteoporosis include fluoride, Vitamin D and calcium supplementation, increased physical activity and estrogen replacement therapy as the primary choice. The precise mechanism of the action of estrogen on bone metabolism is unknown. There are no estrogen receptors which have been identified in bone, and estrogen does not appear to stimulate osteoblastic activity. Estrogen therapy does not replace bone which has already been lost, and if discontinued, more rapid bone loss results.

Because of the potential severity and frequency of postmenopausal complications, long-term estrogen replacement therapy is a frequent practice. However, this has generated a great deal of controversy. Estrogen therapy has been implicated in the development of a variety of disorders. The Boston Collaborative Drug Surveillance Program indicated a summary risk ratio for gallbladder disease in postmenopausal women taking estrogen of 2.5. Boston Collab. Drug Surv., "Surgically Confirmed Gallbladder Disease, Venous Thromboembolism, and Breast Tumors in Relation to Postmenopausal Estrogen Therapy," *N. Eng. J. Med.* 290:15–19 (1974). Other studies have reported an association of estrogen replacement with hypertension, abnormal glucose tolerance, hypercoagulable states and arteriosclerosis, although these observations have not been confirmed, M. Crane, et al., "Hypertension, Oral Contraceptive Agents, and Conjugated Estrogens," *Ann. Int. Med.* 74(1):13–21 (1971); R. Pfeffer, "Estrogen Use, Hypertension and Stroke in Postmenopausal Women," *J. Chron. Dis.* 31:389–398 (1978); M. Notelovitz, "Metabolic Effect of Conjugated Oestrogens (USP) on Glucose Tolerance," *So. African Med. J.* 48(4):2599–2603 (1974); J. Stangel, et al., "The Effect of Conjugated Estrogens on Coagulability in Menopausal Women," *Obstet. Gynecol.* 49(3):314–316 (1977); T. Gordon, et al., "Menopause and Coronary Heart Disease," *Ann. Int. Med.* 89(2):157–161 (1978).

A role of estrogen in the development of benign breast disease has been suggested. The presence of estrogen receptors in the breast has been well documented, and estrogen may induce cystic or dysplastic changes demonstrated by mammography in postmenopausal women. Estrogen can induce mammary tumors in animals, particularly in susceptible strains of mice and rats. Some breast cancers in women respond to oophorectomy, suggesting a role in humans of estrogen in the stimulation and maintenance of breast neoplasia.

Unopposed estrogenic stimulation has also been implicated in the development of endometrial hyperplasia and endometrial carcinoma. Progestins given regularly and for a sufficient length of time appear to be protective against endometrial cancer. Postmenopausal women treated with estrogen-progestin combinations, however, frequently experience regular uterine bleeding which is unacceptable to many of them. For these reasons, an alternative to estrogen replacement therapy would have wide-spread application.

Efforts to counteract the ill effects of estrogen therapy include estrogen therapy coupled with short periods of antiestrogen supplementation. See A. Kauppila, et al., "Comparison of Megestrol Acetate and Clomiphene Citrate as Supplemental Medication in Postmenopausal Oestrogen Replacement Therapy," *Arch. Gynecol.* 234:49–58 (1983). In his study, Kauppila administered 1.25 mg/day conjugated oestrogens to postmenopausal women for 20 days. These 20 days were followed by a pause of 10 days. During every third pause, either 10 mg of megestrol acetate or 50 mg of clomiphene citrate, U.S. Pat. No. 2,914,563, was administered daily for 10 days. See also U.S. Pat. Nos. 4,061,733; 2,914,562; 2,914,564; and 3,634,517. Similar tests were reported by A. Kauppila, M.D., et al., "Postmenopausal Hormone Replacement Therapy With Estrogen Periodically Supplemented With Antiestrogen," Am. J. Obstet. Gynecol. 140(7):787–792 (1981). See also A. Wise, et al., "Quantitative Relationships of the Pituitary-Gonadal Axis in Postmenopausal Women," J. Lab. Clin. Med., 81(1):28–36 (1973). These studies used estrogen as a part of the treatment.

The literature is replete with studies of the activity of antiestrogens in varying situations. See E. Su-Rong Huang and W. Miller, "Estrogenic and Antiestrogenic Effects of Enclomiphene and Zuclomiphene on Gonadotropin Secretion by Ovine Pituitary Cells in Culture," Endocrinology 112(2):442–448 (1983); A. Mukku, et al., "Stimulatory and Inhibitory Effects of Estrogen and Antiestrogen on Uterine Cell Division,"Endocrinology 109(4):1005–1010 (1981); M. Sankaran and M. Prasad, "A Critique on the Evaluation and Mode of Action of Antiestrogens", Hormones and Antagonists. Gynec. Invest. 3:143–147 (1972); L. Terenius and I. Ljungkvist, "Aspects on the Mode of Action of Antiestrogens and Antiprogestogens," Hormones and Antagonists. Gynec. Invest. 3:96–107 (1972); C. Geynet, et al., "Estrogens and Antiestrogens," Hormones and Antagonists. Gynec. Invest. 3:2–29 (1972); J. Wood, et al., "Estrogenic and Antiestrogenic Effects of Clomiphene, MER-25 and CN-55,945 -27 on the Rat Uterus and Vagina," Endocrinol. 82:69–74 (1968); K. Schulz et al., "Studies on Anti-Oestrogenic and Oestrogen-Like Action of Clomiphene Citrate—Animal Experiments," Hormones and Antagonists. Gynec. Invest. 3:135–141 (1972); J. Clark and B. Markaverich, "The Agonistic-Antagonistic Properties of Clomiphene: A Review," Pharmac. Ther. 15:467–519 (1982). See also, M. Pugeat, et al., "On Testing The Threshold of Sensitivity of the Gonadostate in the Late Menopausal Period: Effect of the Administration of Clomiphene Citrate or Ethynylestradiol on Plasma Levels of Gonadotropin, Testosterone and Delta-4 Androstendione," Eur. J. Obstet. Gynecol. Reprod. Biol. 9(3)-218-219 (1979); M. Zambrano, et al., "Evaluation of the Action of Clomiphene Citrate (Clomid) on Mouse Chromosomes by the Metaphase and Micronucleus Tests," Rev. Brasil. Genet. 2:339–344 (1982); J. Gennes, et al., "Clinical, Biological, Histological and Genetic Studies of De Morsier's Syndrome (Hypogonadotrophic Hypogonadism With Anosmia)", Ann. Endrocrinol. 31(5):841–861 (1970); I. Spita, et al., "The Decreased Basal and Stimulated Prolactin Levels in Isolated Gondotrophin [sic] Deficiency: A Consequence of the Low Oestrogen State," Clinical Endocrinology 16:423–432 (1982); S. Aksel, M.D., and G. Jones, M.D., "Etiology and Treatment of Dysfunctional Uterine Bleeding," J. Obstet. and Gynec. 44(1):1–13 (1974); T. Hashimoto, M.D., et al., "Endocrinological Study of Patients With Meningitis Tuberculosa," Jap. J. Med. 20(1):45–49 (1981); and, C. March, M.D., "Effect of Pretreatment with Clomiphene Citrate Upon Human Menopausal Gonadotropin Therapy for Anovulation, " Fertil. Steril. 26(2):191–192 (1975).

Many writers observed that some antiestrogens had weak estrogenic effects. Apparently due to concern about the compounded estrogenic effect which might arise when estrogen and weakly estrogenic antiestrogens are administered together, antigonadotropic agents which were substantially free from estrogenic effects began to appear, as shown in U.S. Pat. No. 3,843,727 and U.S. Pat. No. 3,697,581. These nonestrogenic antiestrogens were developed for administration along with estrogen to counteract the harmful effects of estrogen therapy.

Some researchers took an objective interest in the weak estrogenic effect of antiestrogens. See, T. Hashimoto, M.D., et al., "Dual Effect of Clomiphene Citrate on Pituitary Gonadotropin Secretion in Postmenopausal Women," Endocrinol. Jap. 23(2):115–118 (1976); T. Nencioni, et al., "Plasma FSH, LH and Prolactin Levels in Postmenopausal Women Undergoing Cyclofenil [sic] Treatment," Acta Obstet. Gynecol. Scand. 61:487–490 (1982); R. Young, et al., "Antiestrogen Effects on Gonadotropins and Uterus in the Ovariectomized Rat," Abstracts of the Endocrine Society #142, p. 108 (1979). But see, J. Clark, et al., "The Agonistic-Antagonistic Properties of Clomiphene: A Review," Pharmac. Ther. 15:467-519 (1982), in which the use of clomiphene is warned against; see also M. Pugeat, et al., "Effects of Clomiphene and Estrogens on Circulating Gonadotropins, Testosterone, Androstenedione, in Old Menopausal Women," Ann. Endocrinol. 38:363-365 (1977). One group studied the effects of the antiestrogen clomiphene in total body calcium in rats. A. LeBlanc, et al., "Effects of Clomiphen on Total Body Calcium in Aged Oophorectomized Rats," Calcium, Calcium Hormones, Abstract #7738, p. 1594 (1982).

In spite of all of the literature, there is currently no treatment for postmenopausal symptoms in which estrogen is not administered. A regime including estrogen may be workable for those women having only minor contraindications to estrogen therapy; however, for some women, estrogen is absolutely contraindicated. For these women, there is presently no satisfactory treatment.

SUMMARY OF THE INVENTION

The present invention provides a method of treating postmenopausal symptoms without using estrogen.

According to the invention, postmenopausal or estrogen deficient subjects are administered a dose of a true antiestrogen, on a regular basis for an extended period of time, in the absence of administration of estrogen. As a result of this treatment, the symptoms secondary to estrogen deficiency will be alleviated without the ill effects of estrogen therapy.

DESCRIPTION OF THE PREFERRED EMBODIMENTS

A "true" antiestrogen differs from the nonestrogenic antiestrogens as discussed, for example, in U.S. Pat. Nos. 3,843,727 and 3,697,581, in that it has weak estrogenic effects. A "true" antiestrogen binds estrogen receptors, competing with estrogen therefor. In the presence of estrogen, a true antiestrogen inhibits estrogenic effects. In the progressive absence of estrogen, true antiestrogens exhibit progressively stronger estrogenic effects.

In a preferred embodiment of the present invention, a true antiestrogen, preferably zuclomiphene citrate or clomiphene citrate, is administered to an estrogen deficient subject, e.g., a postmenopausal woman or an oophorectomized woman. The true antiestrogen may be administered in a variety of ways, such as injection, food supplementation, etc., a preferred form of administration being tablets. The true antiestrogen is administered on a regular basis, depending upon the period the true antiestrogen remains active in the subject's system. The true antiestrogen may only be needed weekly or monthly; however, the invention also contemplates administration of the antiestrogen more frequently, up to several times a day, depending upon the patient's needs and capacity for the drug, and upon the characteristics of the particular drug. Each dose of true antiestrogen preferably is 0.4–3.0 micromoles/kg body weight, or more preferably 0.7–2 micromoles/kg. body weight.

The true antiestrogen of this invention may be any one of the following compounds:

Cycladiene, Merck Index, 10th ed. #3085 and U.S. Pat. No. 2,464,203 and U.S. Pat. No. 2,465,505, incorporated herein by reference;

Tamoxifen, Merck Index, 10th ed. 190 8923, incorporated herein by reference;

Nafoxidine, USAN and USP Dictionary of Drug Names, p. 327 (1983), incorporated herein by reference;

CI-680, Unlisted Drugs, 28(10):169(o) (1976), incorporated herein by reference;

CI-628, Unlisted Drugs, 26(7):106(1) (1974), incorporated herein by reference;

CN-55,945-27, or nitromifene citrate, Unlisted Drugs, 27(12):194(n) (1975), incorporated herein by reference;

R2323 or 13-ethyl-17a-ethynl-17B-hydroxygona-4,9,11-triene-3-one, Unlisted Drugs, 23(3):34(b) (1971), incorporated herein by reference;

MER-25; U-11,555A; U-11,100A; ICI-46,669 and ICI-46,474; L all shown in L. Terenius, et al., "Aspects on the Mode of Action of Antiestrogens and Antiprogestogens, Hormones and Antagonists. Gynec. Invest. 3:98, incorporated herein by reference;

Compounds having the formula:

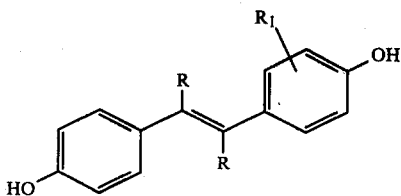

wherein $R_1$ can be hydrogen, an aromatic group or an alkyl group, the alkyl group preferably having no more than 9 carbon atoms, and R can be an aromatic group or an alkyl group, the alkyl group preferably having no more than 9 carbon atoms, the derivatives of this invention including only those derivatives exhibiting true antiestrogenic effects and not including diethylstilbestrol, wherein both R's are an ethyl group, and $R_1$ is a hydrogen group;

Diphenol hydrochrysene; erythro-MEA; and Park Davis CN-55,945; all disclosed in C. Geynet, et al., "Estrogens and Antiestrogens," Hormones and Antagonists. Gynec. Invest. 3:12–13 (1972), incorporated herein by reference;

Allenolic acid and cyclofenyl, disclosed in C. Geynet, et al., Hormones and Antagonists. Gynec. Invest. 3:17 (1972), incorporated herein by reference;

Chlorotrianisene, Merck Index, 10th ed., #2149, incorporated herein by reference;

Ethamoxytriphetol, Merck Index, 10th ed., #3668, incorporated herein by reference;

Triparanol, Merck Index, 10th ed., #9541 and U.S. Pat. No. 2,914,562, incorporated herein by reference; or Any of the triphenyl compounds shown in U.S. Pat. No. 2,914,563, hereby incorporated by reference, which discloses compounds having the formula

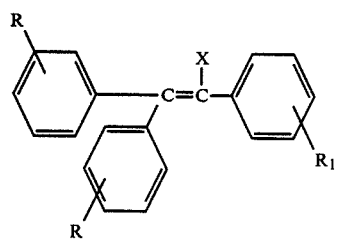

wherein one of the R's is a basic ether of the formula —$OC_nH_{2n}$—A wherein n is 2, 3 or 4, and A is a diaklylamino group of 1–4 carbon atoms or N-piperidyl or B-morpholinyl, and the other R and $R_1$ are hydrogen, halogen or methoxy and X is halogen.

Despite the heterogeneity in the chemical configuration of true antiestrogens, these compounds have a common mode of action. See, M. Sankaran and M. Prasad, "A Critique on the Evaluation and Mode of Action of Antiestrogens," Hormones and Antagonists. Gynec. Invest. 3:142–147 (1972), an L. Terenius and I. Ljungkvist, "Aspects on the Mode of Action of Antiestrogens and Antiprogestogens," Hormones and Antagonists. Gynec. Invest. 3:96–107 (1972).

The estrogenic activity of these weakly estrogenic true antiestrogens manifests itself more strongly as the bodily estrogen levels decrease. In those women who cannot take estrogen and have no bodily estrogen production, the true antiestrogen will exhibit its strongest estrogenic effects. These beneficial estrogenic effects will be achieved in the absence of the harmful effects of estrogen discussed above. Not only will the harmful side effects of estrogen be avoided, but also many true antiestrogens have been used as therapeutic agents to help treat the side effects of estrogen. This therapeutic value is an added advantage of the treatment embodied in the invention.

A preferred embodiment of the present invention is illustrated in the following example:

EXAMPLE 1

Twenty postmenopausal or castrate females will be randomly assigned to one of two groups. Patients in one group will receive cyclic estrogen replacement therapy. Patients in the second group will be treated with clomiphene citrate at 12.5 mg/day or 25 mg/day. A typical patient will be a postmenopausal woman, 60 years of age, approximately 130 lbs. None of the subjects will have had: (1) prior treatment with estrogenic agents less than sixty (60) days prior to treatment; (2) a history of endometrial or breast cancer; (3) a previous hysterectomy less than sixty (60) days prior to treatment; (4) a significant underlying disease which might interfere with evaluation of the patient's response to therapy; or (5) a history of thromboembolism.

Clomiphene citrate is a racemic mixture having the following structure:

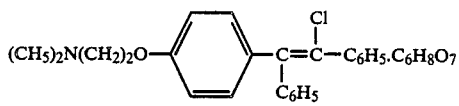

No estrogen will be administered to those subjects receiving clomiphene citrate. The clomiphene citrate and cyclic estrogens will be administered daily for three months.

During those three months, baseline measurements in both groups will include 24-hour urinary estrogen, hydroxyproline, creatinine excretion, serum LH, FSH, cholesterol, high density lipoprotein, ionized calcuim, parathyroid hormone (PTH), calcitonin, SMA-6 and SMA-12, blood pressure, weight, vaginal cytology and endometrial histology. Photon absorptiometry will be performed for determining bone density if possible. Subjects will be hospitalized and a fed a protein-free diet prior to collection of the 24-hour urine sample. All blood samples for PTH will be collected between 8:00 a.m. and 10:00 a.m. To avoid error secondary to diurnal variations. Menopausal symptoms will be quantitated using the Kupperman Menopausal Index, H. Kupperman, et al., "Comparative Clinical Evaluation of Estrogenic Preparations by the Menopausal and Amenorrheal Indices," *J. Clin. Endo.* 13:688–703 (1953), incorporated herein by reference. The symptoms used in devising the Index are as follows: vasomotor complaints, paresthesia, insomnia, nervousness, melancholia, weakness or fatigue, palpitation and formication. These symptoms will be quantitated at monthly intervals.

At the end of three months, it is expected that the above-described Kupperman symptoms, being symptoms secondary to estrogen deficiency, will be alleviated by clomiphene citrate to an extent at least comparable to the relief experienced by the patients undergoing estrogen therapy.

Further, clomiphene citrate has been demonstrated to maintain the level of total body calcium in ovariectomized rats at levels similar to the levels retained by estrogen-producing rats. Estrogen deficient rats not receiving clomiphene citrate, however, experience bone loss. See P. Beall, L. Misra, R. Young, H. Spjut, H. Evans and A. LeBlanc, "Clomiphene Protects Against Osteoporosis in the Mature Ovariectomized Rat," *Calcif. Tissue Int'l.* 36:123–125 (1984). The same relief of bone loss should occur in postmenopausal women and castrate women who are also estrogen deficient. The administration of clomiphene citrate should prevent bone loss or osteoporosis from the time the treatment is begun.

The dosage of clomiphene citrate in Example 1 can range from 12.5–100 mg.

EXAMPLE 2

Following the procedure of Example 1, clomiphene citrate is replaced by 12.5–100 mg/day of zuclomiphene citrate, the cisisomer of clomiphene citrate, having the following structure:

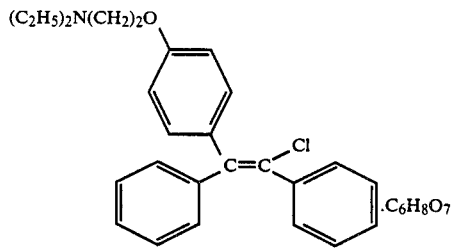

Results similar to those achieved in Example 1 are expected, i.e., estrogen deficient subjects undergoing zuclomiphene citrate therapy should be relieved of secondary estrogen deficiency symptoms in a manner comparable to the relief achieved with estrogen therapy.

Various modifications of the process and compositions of the invention may be made without departing from the spirit thereof and it is to be understood that the invention is to be limited only as defined in the following claims.

I claim:

1. A method of treating menopausal symptoms comprising administering a true antiestrogen to a postmenopausal or an oophorectomized woman in a dose effective to prevent the manifestation of said menopausal symptoms, without any estrogen administration.

2. The method according to claim 1 wherein said antiestrogen is administered as often as needed to prevent said symptoms.

3. The method according to claim 2 wherein said dose is between 0.4–3.0 micromoles/kg body weight.

4. The method according to claim 3 wherein said antiestrogen is nafoxidine.

5. The method according to claim 2 wherein said antiestrogen is tamoxifen.

6. The method according to claim 1 wherein said antiestrogen is cycladiene.

7. The method according to claim 1 wherein said antiestrogen is CI-680.

8. The method according to claim 1 wherein said antiestrogen is CI-628.

9. The method according to claim 1 wherein said antiestrogen is CN-55,945–27.

10. The method according to claim 1 wherein said antiestrogen is MER-25.

11. The method according to claim 1 wherein said antiestrogen is U-11,555A.

12. The method according to claim 1 wherein said antiestrogen is U-11,100A.

13. The method according to claim 1 wherein said antiestrogen is ICI-46,669.

14. The method according to claim 1 wherein said antiestrogen is ICI-46,474.

15. The method according to claim 1 wherein said antiestrogen is a compound having the formula

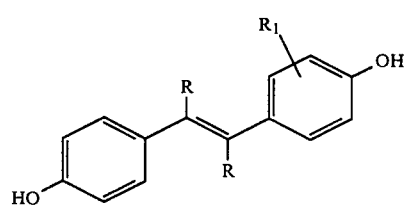

wherein $R_1$ may be selected from the group consisting of hydrogen, an aromatic group and an alkyl group and R can be selected from the group consisting of an aromatic group and an alkyl group.

16. The method according to claim 15 wherein said R alkyl groups contain no more than 9 carbon atoms.

17. The method according to claim 1 wherein said antiestrogen is diphenolhydrochrysene.

18. The method according to claim 1 wherein said antiestrogen is erythro-MEA.

19. The method according to claim 1 wherein said antiestrogen is Parke Davis CN-55,945.

20. The method according to claim 1 wherein said antiestrogen is allenolic acid.

21. The method according to claim 1 wherein said antiestrogen is cyclofenil.

22. The method according to claim 1 wherein said antiestrogen is chlorotrianisene.

23. The method according to claim 1 wherein said antiestrogen is ethyamoxytriphetol.

24. The method according to claim 1 wherein said antiestrogen is triparanol.

25. The method according to claim 1 wherein said antiestrogen is a compound having the formula

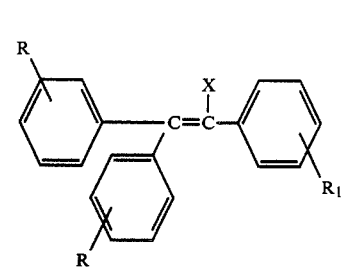

wherein one of the R's is a basic ether of the formula $-OC_nH_{2n}-A$ wherein n is 2, 3 or 4, and A is a dialkyl amino group of 1-4 carbon atoms or N-piperidyl or B-morpholinyl, and the other R and $R_1$ are selected from the group consisting of hydrogen, halogen and methoxy and X is halogen.

26. The method according to claim 1 wherein said antiestrogen is clomiphene citrate.

27. The method according to claim 1 wherein said antiestrogen is zuclomiphene citrate.

28. A method of treating menopausal symptoms comprising administering 12.5 mg-100 mg of clomiphene citrate to a post menopausal or an oophorectomized woman as often as needed to prevent said symptoms, without estrogen administration.

29. A method of treating menopausal symptoms comprising administering 12.5 mg-100 mg of zuclomiphene citrate to a post menopausal or an oophorectomized woman as often as needed to prevent said symptoms, without estrogen administration.

* * * * *